United States Patent
Rumpf et al.

(10) Patent No.: US 7,959,766 B2
(45) Date of Patent: Jun. 14, 2011

(54) METHOD FOR OBTAINING CYCLODODECATRIENE BY EVAPORATION

(75) Inventors: Bernd Rumpf, Hockenheim (DE); Ortmund Lang, Quirnbach (DE); Andrea Haunert, Mannheim (DE); Thomas Genger, Lambsheim (DE); Anton Meier, Birkenheide (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 561 days.

(21) Appl. No.: 11/994,122

(22) PCT Filed: Jun. 30, 2006

(86) PCT No.: PCT/EP2006/063746
§ 371 (c)(1),
(2), (4) Date: Dec. 28, 2007

(87) PCT Pub. No.: WO2007/003602
PCT Pub. Date: Jan. 11, 2007

(65) Prior Publication Data
US 2008/0217158 A1   Sep. 11, 2008

(30) Foreign Application Priority Data

Jul. 5, 2005   (DE) .................. 10 2005 031 316

(51) Int. Cl.
*B01D 3/04* (2006.01)
*C07C 7/04* (2006.01)
*C07C 13/277* (2006.01)

(52) U.S. Cl. ............. 203/29; 159/47.1; 203/40; 203/49; 203/78; 585/20; 585/803; 585/809

(58) Field of Classification Search .................... 159/15, 159/26.1, 47.1, DIG. 8, DIG. 10; 203/2, 203/3, 29, 40, 49, 78; 585/20, 803, 809
See application file for complete search history.

(56) References Cited

U.S. PATENT DOCUMENTS

| 3,365,507 A | 1/1968 | Rike, III |
| 3,550,669 A * | 12/1970 | Casper et al. .................. 159/6.1 |
| 3,969,196 A * | 7/1976 | Zosel ............................ 203/49 |
| 7,649,119 B2 * | 1/2010 | Teles et al. .................... 568/363 |
| 2007/0178029 A1 * | 8/2007 | Goebbel et al. ............... 422/227 |

* cited by examiner

*Primary Examiner* — Virginia Manoharan
(74) *Attorney, Agent, or Firm* — Oblon, Spivak, McClelland, Maier & Neustadt, L.L.P.

(57) ABSTRACT

Process for recovering cyclododecatriene (CDT) from a solution containing CDT and high boilers such as deactivated catalyst and polymers, which includes feeding the solution into a preheater and heating it, subsequently depressurizing it through a downstream pressure maintenance device and feeding the resulting two-phase mixture into a helical tube evaporator and there reducing the CDT content of the liquid phase by partial evaporation and discharging a gaseous product stream having an increased concentration of CDT.

27 Claims, 1 Drawing Sheet

METHOD FOR OBTAINING CYCLODODECATRIENE BY EVAPORATION

The present invention relates to a process for recovering cyclododecatriene (CDT) from a solution comprising CDT and high boilers such as deactivated catalyst, salts and polymers.

Cyclododecatriene is a valuable intermediate for the preparation of high-grade plastics such as Nylon 6.6, Nylon 6.12, polyesters or polyamides.

The preparation of cyclododecatriene is described, for example, in Ullmann's Encyclopedia of Industrial Chemistry, Fifth Edition, Volume A8, 205-207. For this purpose, butadiene is cyclotrimerized in the presence of catalysts comprising Ti, Cr or Ni. The yield of this reaction is typically better than 80% by weight, and by-products obtained are, in particular, dimers and oligomers of butadiene. Before further purification and work-up of the desired product, the catalyst has to be deactivated. This can be effected by, for example, addition of an aqueous solution of sodium hydroxide.

To work up the desired product CDT, the dimers and oligomers and also the deactivated catalyst firstly have to be removed. For this purpose, this liquid product stream, hereinafter also referred to as "output from the reaction", is partially evaporated in a suitable evaporator system. The vapor formed comprises the desired product, and the high-boiling bottom product is, for example, utilized thermally. In the subsequent work-up steps, the desired product is purified further.

Owing to the thermal sensitivity of the desired product CDT, the removal of high boilers has to be carried out at very short residence times and low temperatures. Preference is therefore given to using thin film evaporators or short path evaporators, if appropriate in combination with an upstream falling film evaporator, forced circulation evaporator or forced circulation flash evaporator. A corresponding apparatus and process concept (use of a thin film evaporator) is disclosed, for example, in the U.S. Pat. No. 3,365,507.

However, owing to the apparatuses used, the process is complicated in process engineering terms. Other disadvantages of this apparatus concept are the comparably high capital costs for the combination of falling film evaporator and thin film evaporator and the high variable costs for the operation of the thin film evaporator. Furthermore, the use of evaporator types such as falling film evaporators, forced circulation evaporators and forced circulation flash evaporators is associated with considerable process engineering risks, since the high-boiling components present in the feed stream and the decomposition products which may be formed during evaporation tend to form deposits on hot surfaces. In addition, the formation of deposits can also occur in thin film evaporators, e.g. on the internal wiper system, which can lead to production stoppages.

It was therefore an object of the present invention to discover a process for evaporating the desired product CDT from the output from the reaction, which gives CDT in equal or improved quality in respect of color, color stability, odor and purity while avoiding the abovementioned disadvantages. In addition, the losses of desired product due to residual contents in the bottoms were to be minimized.

We have accordingly found a process for recovering cyclododecatriene (CDT) from a solution comprising CDT and high boilers such as deactivated catalyst and polymers, which comprises feeding the solution into a preheater and heating it, subsequently depressurizing it through a downstream pressure maintenance device and feeding the resulting two-phase mixture into a helical tube evaporator and there reducing the CDT content of the liquid phase by partial evaporation and discharging a gaseous product stream having an increased concentration of CDT.

It has astonishingly been found that the removal of high boilers can, according to the invention, be carried out in a comparatively simply constructed apparatus, viz. a helical tube evaporator (HTE), without external mixing of the liquid film while avoiding formation of deposits on the heated walls. This would not have been expected by a person skilled in the art since, compared to conventional thin film evaporators, significantly greater heat fluxes and, resulting therefrom, significantly greater driving temperature differences are present in a helical tube evaporator, which usually results in an increase in polymerization and deposit formation.

Helical tube evaporators are generally known and are described, for example, in the U.S. Pat. No. 3,550,669. This patent application describes an evaporation apparatus in which the mechanical force required for keeping the heat exchange surface free is provided not by rotating internals but by flow forces. This evaporation apparatus comprises only a single, helically coiled tube which is heated externally. This single-tube evaporator is then operated by feeding the solution or suspension in superheated form under pressure into the apparatus so that part of the volatile constituents of the solution evaporate right at the beginning of the apparatus. This vapor takes on the task of transporting the increasingly viscous solution or suspension through the apparatus and keeps the heat exchange surface free.

Figure 1:
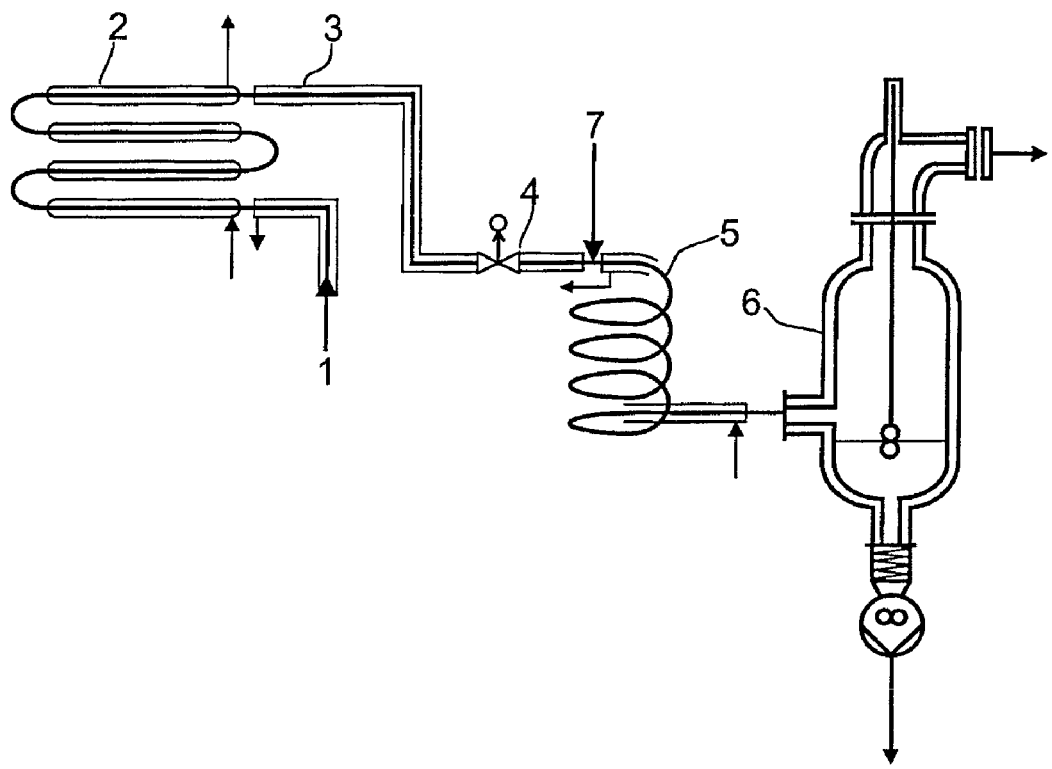
FIG. 1 shows an apparatus which may be used to carry out an embodiment of the invention.

The process of the invention is described in more detail by way of example below with reference to the FIGURE.

The solution to be worked up (output from the reaction) having a concentration of CDT of typically 20-80% by weight (and further comprising solvent (toluene), high boilers (polymers), deactivated catalyst) is fed via line (1) into a preheater (2) operated, for example, by means of heat transfer oil and is heated. The preheating is, depending on the pressure, usually to from 80° C. to 250° C. The heated solution is discharged from the preheater via line (3). The pressure in the preheater is set by means of a downstream pressure maintenance valve (4) so that evaporation of the solution does not take place at any point in the preheater. As preheaters, it is possible to use conventional types of apparatus such as shell-and-tube apparatuses, plate heat exchangers, spiral heat exchangers or the like. The heated solution is depressurized downstream of the pressure maintenance valve (4) and fed into the externally heated helical tube evaporator (5).

The product temperature in the helical tube evaporator is, depending on the pressure, usually in the range from 100° C. to 270° C.

A wave-like film flow is produced in the tube by appropriate selection of the geometry, the total flow and the proportion of gas after depressurization. Intensive heat and mass transfer is achieved in this way. High shear stresses occur at the wall as a result of the high throughputs, so that the buildup of caked material on the heated walls is avoided effectively.

The evaporation ratio to be achieved and thus the concentration of the desired product in the bottom product is determined by the choice of heating temperature and of the pressure in the downstream vapor separator and can, for example, be determined by experiment. For the present purposes, the evaporation ratio is the ratio of amount of distillate to amount of feed.

The helical tube evaporator can, for example, be heated by means of condensing steam or by means of a heated oil circuit. Electric heating is also possible.

Addition of other vapor or inert gas via line (7) enables the partial pressure of the vaporizable component to be reduced and the gas velocity to be increased.

This can be advisable in order to achieve the desired flow regime in the helical tube evaporator or to set the residence time of the solution in the helical tube evaporator or to remove residual low boilers from the solution by stripping. The amount of stripping gas fed into the helical tube evaporator is from 0 to 50% by weight, based on the total feed stream (product+stripping gas), preferably from 0 to 20% by weight.

In a downstream vapor separator (6), liquid and gas are separated from one another. The vapor stream can be condensed in conventional condensers, e.g. shell-and-tube apparatuses or quench condensers. The condensates obtained, which comprise essentially the desired product CDT, can be worked up in conventional distillation apparatuses or can directly be used further. The concentration of CDT in the condensate is usually from 40 to 90% by weight.

The bottom stream from the vapor separator comprises essentially the high boilers formed in the reaction and deactivated catalyst, and the content of desired product is, depending on the mode of operation, less than 20% by weight of CDT, preferably less than 5% by weight, particularly preferably less than 1% by weight of CDT. It is even possible to achieve residual CDT contents of less than 0.5% by weight.

The pressure in the vapor space is set to from 1 to $10^4$ mbar, preferably from 1 to $10^3$ mbar, particularly preferably from 1 to 200 mbar. In the case of relatively demanding requirements, a pressure of from 1 to 100 mbar can be particularly useful here.

In an embodiment of the invention the process includes introducing the cyclododecatriene-reduced liquid phase and the cyclododecatriene-containing gaseous phase into a downstream vapor separator and separating the liquid phase from the gaseous phase at a pressure of from 1 to 400 mbar.

In general, the residence time can be set by means of the flow velocity or the geometry of the helical tube evaporator (diameter and length). The residence time in the helical tube evaporator and the associated piping system is advantageously limited to from 0.5 to 10 minutes, preferably from 0.5 to 2 minutes. Possible further polymerization and thermal decomposition of the desired product are reduced in this way.

The process is generally carried out continuously, but it is in principle also possible to carry out the separation batchwise.

It is likewise possible to connect a plurality of helical tube evaporators in series to form an evaporator cascade and to evaporate the inflowing product stream in a plurality of stages. In this variant, it can be advantageous to operate the evaporator cascade at different pressures. If appropriate, the evaporation stage can also be operated with partial thermal integration. The choice of the different pressure levels of the evaporation stages can be determined by a person skilled in the art by means of calculations and/or by experiment.

In an embodiment of the invention the helical tube evaporator comprises at least two helical tube evaporators connected in series forming an evaporator cascade.

It is also possible to recirculate part of the liquid stream taken off from the helical tube evaporator to the helical tube evaporator for further evaporation. The purification can be improved further in this way.

Furthermore, it can be useful to provide the helical tube with internal and/or external ribs. By this is meant the provision of ribs on the internal or external side of the helical tube, which has the advantage that the performance of the helical tube is improved thereby. This improvement is brought about both by the provision of a larger heat transfer area and by the generation of additional turbulence. Furthermore, the interior of the helical tube can be provided wholly or partly with knitted wire mesh. By this is meant the introduction of knitted wire mesh into the helical tube, which improves heat and mass transfer.

Very high area-specific throughputs at low residence times are achieved by appropriate selection of the operating point of a helical tube evaporator. Thus, up to 8 kg/h of a CDT-comprising solution could be processed without problems by passage through a helically coiled tube having an internal diameter of 7 mm in laboratory experiments.

In embodiments of the invention a single pass of the two-phase mixture through the helical tube evaporator forms a cyclododecatriene-reduced liquid phase comprising less than 5% by weight or less than 0.5% by weight of cyclododecatriene.

Owing to the low residence time of the solution at elevated temperatures, the formation of polymers as a result of excessively high thermal stress is prevented effectively in the process of the invention, so that the losses of CDT due to polymerization in the evaporator system remain at less than 1% by weight, contrary to previous experience with conventional evaporator concepts. A new solution for the recovery of CDT which is simple in process engineering terms and gives long periods of operation and has low operating costs together with a small outlay in terms of apparatus is thus provided.

EXAMPLES

Example 1

Not According to the Invention

Concentration of a solution comprising 50% by weight of CDT in a falling film evaporator. The plant was equipped with an evaporator tube having dimensions of 25*2*3000 mm (heat transfer area about 0.2 $m^2$). The pressure in the vapor space was set to 200 mbar. The feed rate was 4 kg/h of product. The inflow temperature of the heat transfer oil used was about 190° C. The evaporation ratio achieved at the beginning of the experiment was about 90%, so that a total loss of desired product in the bottoms of 1% by weight (based on the amount of desired product in the feed) was established. During the course of the experiment, the inflow temperature of the heat transfer oil had to be increased in a plurality of steps to up to 220° C. in order to keep the evaporation ratio approximately constant. The experiment had to be stopped after a running time of 3 days. Severe and irreversible fouling of the evaporator tube was found.

Example 2

According to the Invention

Concentration of a solution comprising 50% by weight of CDT in a helical tube evaporator plant as shown in the FIGURE. The plant was equipped with a glass helix (I=6 m, internal diameter 7 mm, heat transfer area about 0.19 $m^2$). The pressure in the vapor space was set to 200 mbar. The feed rate was 8 kg/h of product. The heating temperature in the pre-heater was 220° C. and in the helical tube was 220° C. The evaporation ratio achieved was 90%, so that a total loss of desired product in the bottoms of 0.8% by weight (based on the amount of CDT in the feed) was established. Irreversible fouling of the heating surfaces was not observed even after a number of days of operation.

The invention claimed is:

1. A process for recovering cyclododecatriene (CDT) from a solution comprising CDT and high boilers such as a deactivated catalyst and polymers, which comprises
   feeding the solution into a preheater and heating the solution, subsequently
   depressurizing the solution through a downstream pressure maintenance device and
   feeding a resulting two-phase mixture into a helical tube evaporator and there
   reducing the CDT content of the liquid phase by partial evaporation and
   discharging a gaseous product stream having an increased concentration of CDT.

2. The process according to claim 1, wherein the proportion of CDT in the liquid phase is reduced to a content of less than 5% by weight of CDT in a single pass through the helical tube evaporator.

3. The process according to claim 1, wherein the proportion of CDT in the liquid phase is reduced to a content of less than 0.5% by weight of CDT in a single pass through the helical tube evaporator.

4. The process according to claim 1, further comprising:
   discharging a liquid stream from the helical tube evaporator,
   wherein part of the liquid stream discharged from the helical tube evaporator is fed back into the helical tube evaporator for further evaporation.

5. The process according to claim 1, wherein valves or restrictors are used in the helical tube evaporator to achieve more intense mixing of the liquid phase.

6. The process according to claim 1, wherein a stripping gas is introduced downstream of the downstream pressure maintenance device.

7. The process according to claim 1, wherein an internally and/or externally ribbed tube is used in the helical tube evaporator.

8. The process according to claim 1, wherein the interior of the evaporator helical tube is provided with a knitted wire mesh.

9. The process according to claim 1, wherein the two-phase stream discharged from the helical tube evaporator is introduced into a downstream vapor separator and the vapor separator is operated at a pressure of from 1 to 400 mbar.

10. The process according to claim 1, wherein the two-phase stream discharged from the helical tube evaporator is introduced into a downstream vapor separator and the vapor separator is operated at a pressure of from 1 to 200 mbar.

11. The process according to claim 1, wherein the gaseous stream discharged from the helical tube evaporator is partially or completely condensed in a condenser.

12. The process according to claim 1, wherein two or more helical tube evaporators are connected in series to form an evaporator cascade and the solution flowing into the evaporator cascade is evaporated in stages.

13. The process according to claim 12, wherein the evaporator cascade is operated at different pressures.

14. The process according to claim 13, wherein the evaporator cascade is operated with thermal integration.

15. A process for recovering cyclododecatriene from a solution comprising cyclododecatriene and one or more high boiler materials, comprising:
    feeding the solution into a preheater to heat the solution and form a heated solution, then
    depressurizing the heated solution through a downstream pressure maintenance device to form a two-phase mixture, then
    feeding the two-phase mixture into a helical tube evaporator to at least partially evaporate the two-phase mixture and form a cyclododecatriene-reduced liquid phase and a cyclododecatriene-containing gaseous product stream, then
    discharging the cyclododecatriene-containing gaseous product stream.

16. The process according to claim 15, wherein a single pass of the two-phase mixture through the helical tube evaporator forms a cyclododecatriene-reduced liquid phase comprising less than 5% by weight of cyclododecatriene.

17. The process according to claim 15, wherein a single pass of the two-phase mixture through the helical tube evaporator forms a cyclododecatriene-reduced liquid phase having a cyclododecatriene content of less than 0.5% by weight.

18. The process according to claim 15, further comprising:
    discharging a portion of the cyclododecatriene-reduced liquid stream from the helical tube evaporator, and
    feeding at least a portion of the cyclododecatriene-reduced liquid stream back into the helical tube evaporator.

19. The process according to claim 15, further comprising:
    introducing a stripping gas into the two-phase mixture downstream of the downstream pressure maintenance device.

20. The processing according to claim 15, wherein the helical tube evaporator comprises one or more of an internally ribbed tube and an externally ribbed tube.

21. The process according to claim 15, wherein the interior of the helical tube evaporator comprises a knitted wire mesh.

22. The process according to claim 15, further comprising:
    introducing the cyclododecatriene-reduced liquid phase and the cyclododecatriene-containing gaseous phase into a downstream vapor separator, and
    separating the liquid phase from the gaseous phase at a pressure of from 1 to 400 mbar.

23. The process according to claim 22, wherein the cyclododecatriene-reduced liquid phase and the cyclododecatriene-containing gaseous phase are introduced into a downstream vapor separator operating at a pressure of from 1 to 200 mbar.

24. The process according to claim 15, wherein the cyclododecatriene-containing gaseous stream is discharged from the helical tube evaporator and subsequently at least partially condensed in a condenser.

25. The process according to claim 15, wherein the helical tube evaporator comprises at least two helical tube evaporators connected in series forming an evaporator cascade.

26. The process according to claim 25, wherein the evaporators of the evaporator cascade is operated at different pressures.

27. The process according to claim 25, wherein the evaporator cascade is operated with thermal integration.

* * * * *